United States Patent [19]
Foguet et al.

[11] Patent Number: 6,005,115

[45] Date of Patent: Dec. 21, 1999

[54] FORMS A AND B OF N-[[[2-[[[2-[(DIAMINOMETHYLENE)AMINO]-4-THIAZOLYL]METHYL ]THIO]ETHYL]AMINO]METHYLENE]-4-BROMO-BENZENESULFONAMIDE

[75] Inventors: Rafael Foguet; Lluis Anglada; José A. Ortiz; Aurelio Sacristan; Josep M. Castello, all of Barcelona, Spain

[73] Assignee: Ferrer Internacional, S.A., Barcelona, Spain

[21] Appl. No.: 08/669,359

[22] PCT Filed: Nov. 4, 1994

[86] PCT No.: PCT/ES94/00109

§ 371 Date: Jul. 3, 1996

§ 102(e) Date: Jul. 3, 1996

[87] PCT Pub. No.: WO96/14306

PCT Pub. Date: May 17, 1996

[51] Int. Cl.[6] .................................................. C07D 277/48
[52] U.S. Cl. ............................................................ 548/205
[58] Field of Search .............................................. 548/205

[56] References Cited

U.S. PATENT DOCUMENTS 4,728,655   3/1988   Foguet et al. ............................ 514/326

FOREIGN PATENT DOCUMENTS 0159012   10/1985   European Pat. Off. .

*Primary Examiner*—Robert Gerstl
*Attorney, Agent, or Firm*—Birch, Stewart, Kolasch & Birch, LLP

[57] ABSTRACT

Two forms of N-[[[2-[[[2-[(diaminomethylene)amino]-4-thiazolyl]methyl]thio]ethyl]amino]methylene]-4-bromo-benzenesulfonamidehave been identified. A process for the preparation of thereof and the use thereof are described.

5 Claims, 5 Drawing Sheets

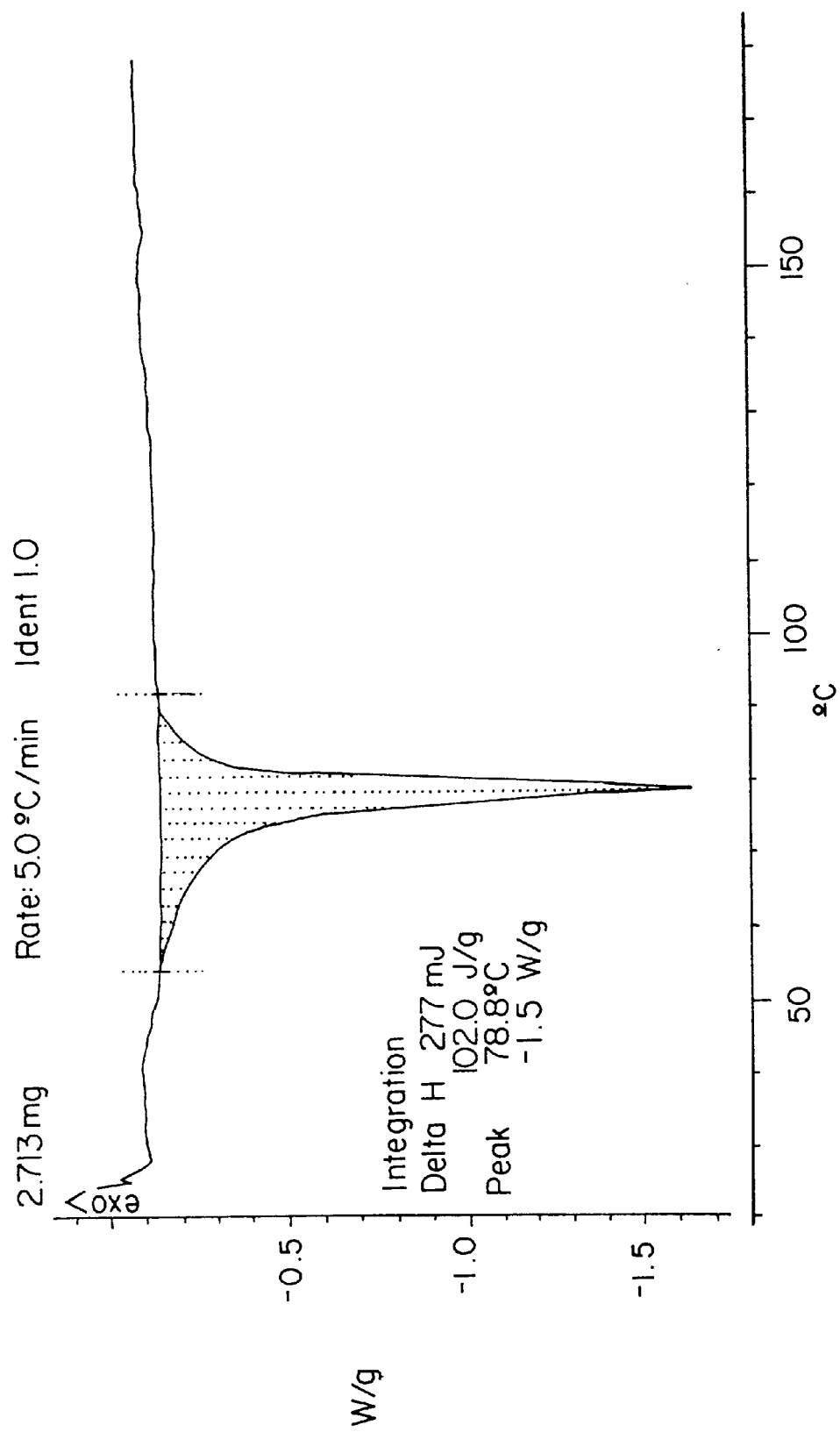

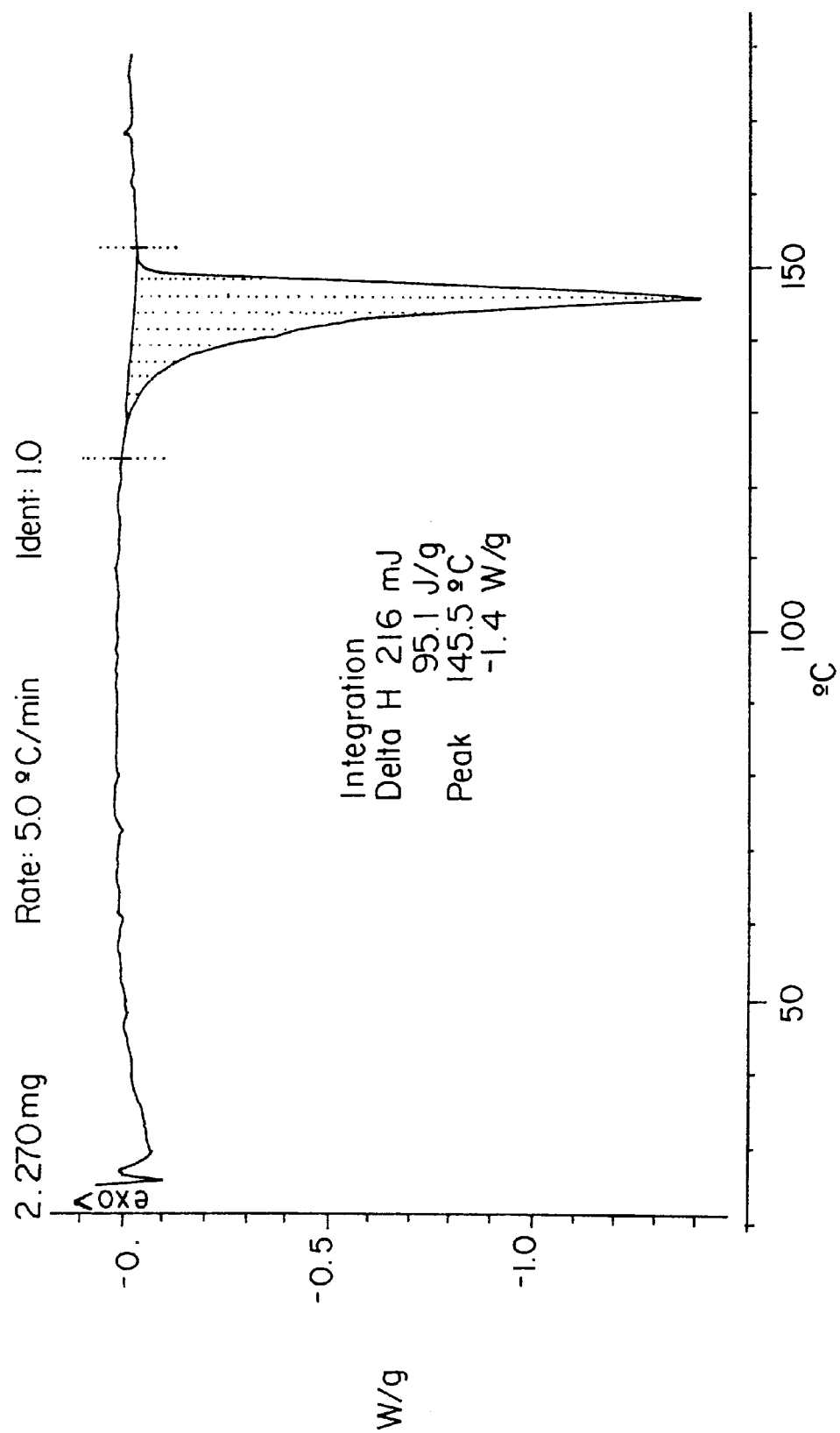

FORMS A AND B OF N-[[[2-[[[2-[(DIAMINOMETHYLENE)AMINO]-4-THIAZOLYL]METHYL]THIO]ETHYL]AMINO]METHYLENE]-4-BROMO-BENZENESULFONAMIDE

The present invention relates to novel Forms A and B of N-[[[2-[[[2-[(diaminomethylene)amino]-4-thiazolyl]methyl]thio]ethyl]]amino]methylene]-4-bromo-benzenesulfonamide-compound known as ebrotidine (WHO).

BRIEF DESCRIPTION OF THE DRAWINGS

FIG. 3 is a differential scanning calorimetry (DSC) thermogram of Ebrotidine Form A.
FIG. 5 is a differential scanning calorimetry (DSC) thermogram of Ebrotidine Form B.

DETAILED DESCRIPTION OF THE INVENTION

Figure 1:
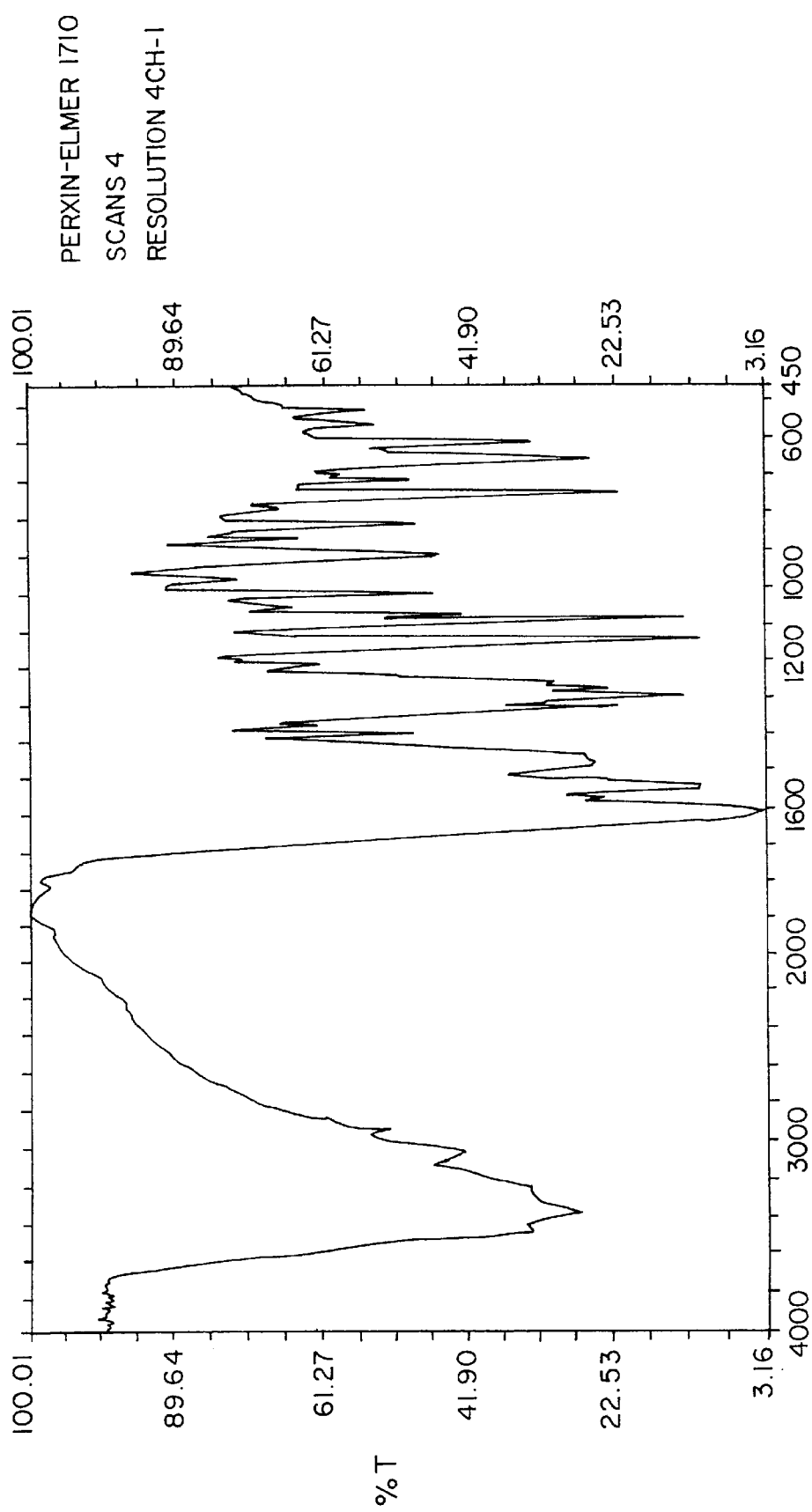
FIG. 1 is an infrared (IR) spectrum of ebrotidine Form A.

N-[[[2-[[[2-[(diaminomethylene)amino]-4-thiazolyl]methyl]thio]ethyl]amino]methylene]-4-bromobenzenesulfonamide, ebrotidine, is a compound which is active as a histamine $H_2$-receptor antagonist, thus becoming useful in therapy as an acid secretion inhibitor. The preparation of this compound was disclosed in European Patent No. 0159012 and U.S. Pat. No. 4728655. The applicants have found out that ebrotidine exhibits two novel forms, A and B, having a melting point in the range of 74–78° C. and 142.5–146° C. respectively. The present invention provides a process for obtaining selectively Forms A and B of ebrotidine. In the aforesaid patents, ebrotidine was obtained with a melting point of 107–110° C. By performing the same experimental method in those patents (Example 23 in both of them), the applicants have found out in the course of different crystallization assays that if to the methanol filtrate resulting from the reaction between [4-[[(2-aminoethyl)thio]methyl]-2-thiazolyl]guanidine and ethyl 4-bromobenzene-sulfonyl-formimidate is added isopropanol and allowed to crystallize, ebrotidine isopropanolate is obtained, which is a useful intermediate for the preparation of Forms A and B of ebrotidine. Thus, the applicants have found out that Form A of ebrotidine can be obtained in a pure state by treating ebrotidine isopropanolate with a mixture of methanol and water. Treatment of the obtained Form A of ebrotidine with methanol leads to Form B of ebrotidine in a pure state. In turn, if Form B of ebrotidine is preferred to be obtained directly from the methanol solution, which is obtained according to the experimental method in the aforesaid example, the medium may be seeded with crystals of Form B, thus constituting an extremely practical variation.

Forms A and B of ebrotidine have different properties. Form A is an amorphous solid and Form B is a crystalline solid. Therefore, Form A is useful to prepare formulations that do not require any compression, such as capsules or sachets, while Form B is useful to prepare tablets. In case that the formulations to be prepared are liquid, the use of either form will be different since the proper characteristics of the solid state are lost in solution.

Forms A and B of ebrotidine mixed with pharmaceutically acceptable carriers can be administered at daily doses ranging from 50 to 2000 mg.

The following examples illustrate the preparation of Forms A and B of ebrotidine, and pharmaceutical formulations containing them. The examples are not intended to limitate the scope of the invention as defined hereinabove or as claimed below.

EXAMPLE 1

N-[[[2-[[[2-[(diaminomethylene)amino]-4-thiazolyl]methyl]thio]ethyl]amino]methylene]-4-bromo-benzenesulfonamide isopropanolate (Ebrotidine isopropanolate)

To a suspension of 44.04 g of [4-[[(2-aminoethyl) thio]methyl]-2-thiazolyl]guanidine dihydrochloride in 100 ml of methanol, 145 ml of 2.05 M methanol potassium hydroxide are added at a temperature below 20° C. To the resultant solution, 42.3 g of ethyl 4-bromobenzene-sulfonyl-formimidate are added at room temperature and the mixture is stirred for 1 hour, cooled at 0–5° C. and filtered. To the filtrate, 245 ml of isopropanol are added at room temperature, and allowed to crystallize for 24 hours to yield 57.9 g of N-[[[2-[[[2-[(diaminomethylene)amino]-4-thiazolyl]methyl]thio]ethyl]amino]methylene]-4-bromo-benzenesulfonamide isopropanolate having the following physico-chemical properties:

Melting point: 96–98° C.

IR (KBr) cm$^{-1}$: 3450 ($NH_2$), 3380 ($NH_2$), 1605 (C=N), 1300 ($SO_2$) and 1180 ($SO_2$).

$^1$H-NMR (DMSO) δ: 1.05 (d, 6H, $(CH_3)_2CH_2OH$), 2.6 (t, 3H, —S—C$\underline{H}_2$—$CH_2$), 3.4 (m, 2H, —S—$CH_2$—C$\underline{H}_2$), 3.54 (s, 2H, het—C$\underline{H}_2$—S), 3.8 (m, 2H, $(CH_3)_2C\underline{H}_2OH$), 6.39 (s, 1H, thiazol), 6.85 (wide, 4H, guanidine), 7.7 (s, 4H, aromatic), 8.15 (s, 1H, NH—C$\underline{H}$=N), 9.05 (wide, 1H, —N$\underline{H}$—CH=).

EXAMPLE 2

N-[[[2-[[[2-[(diaminomethylene)amino]-4-thiazolyl]methyl]thio]ethyl]amino]methylene]-4-bromobenzenesulfonamide Form A (Ebrotidine A form)

57.9 g of N-[[[2-[[[2-[(diaminomethylene)amino]-4-thiazolyl]methyl]thio]ethyl]amino]methylene]-4-bromo-benzenesulfonamide isopropanolate are dissolved in 87 ml of methanol at a temperature ranging between 40 and 50° C. The resultant solution is allowed to stand till a certain degree of turbidity fades away, then filtered and poured onto 550 ml of water at 0–5° C. for 4 hours under energic stirring. After the addition is completed, the mixture is stirred for further 4 hours at 0–5° C. and filtered. The filtrate is washed with abundant water and dried in vacuo at a temperature below 30° C. to yield 49.9 g of ebrotidine Form A.

Melting point: 74–76° C.

IR (KBr) spectrum: FIG. 1

Figure 2A:
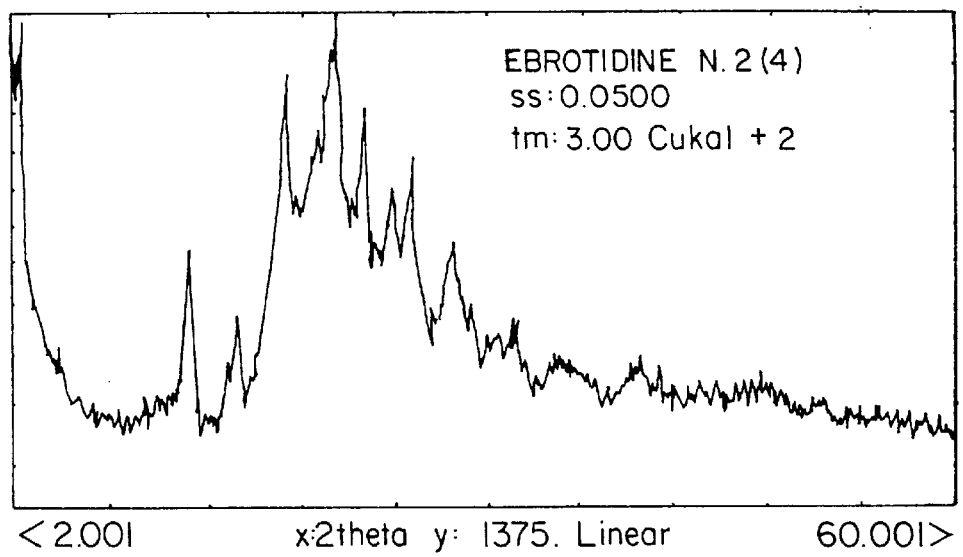
FIG. 2 is an X-ray powder diffractogram of
a) Ebrotidine Form A.
b) Ebrotidine Form B.

X-ray diffractogram: FIG. 2a.

Differential scanning calorimetry thermogram; FIG. 3.

EXAMPLE 3

N-[[[2-[[[2-[(diaminomethylene)amino]-4-thiazolyl]methyl]thio]ethyl]amino]methylene]-4-bromobenzenesulfonamide Form B (Ebrotidine Form B)

a) 49.9 g of ebrotidine Form A are poured onto 245 ml of methanol at 30° C. The resultant suspension is heated at 50–60° C. for 1 hour, and then cooled at room temperature and stirred for 2 hours to yield a solid. The solid is filtered to give 41.9 of ebrotidine Form B.

Melting point: 142.5–146° C.

Figure 4:
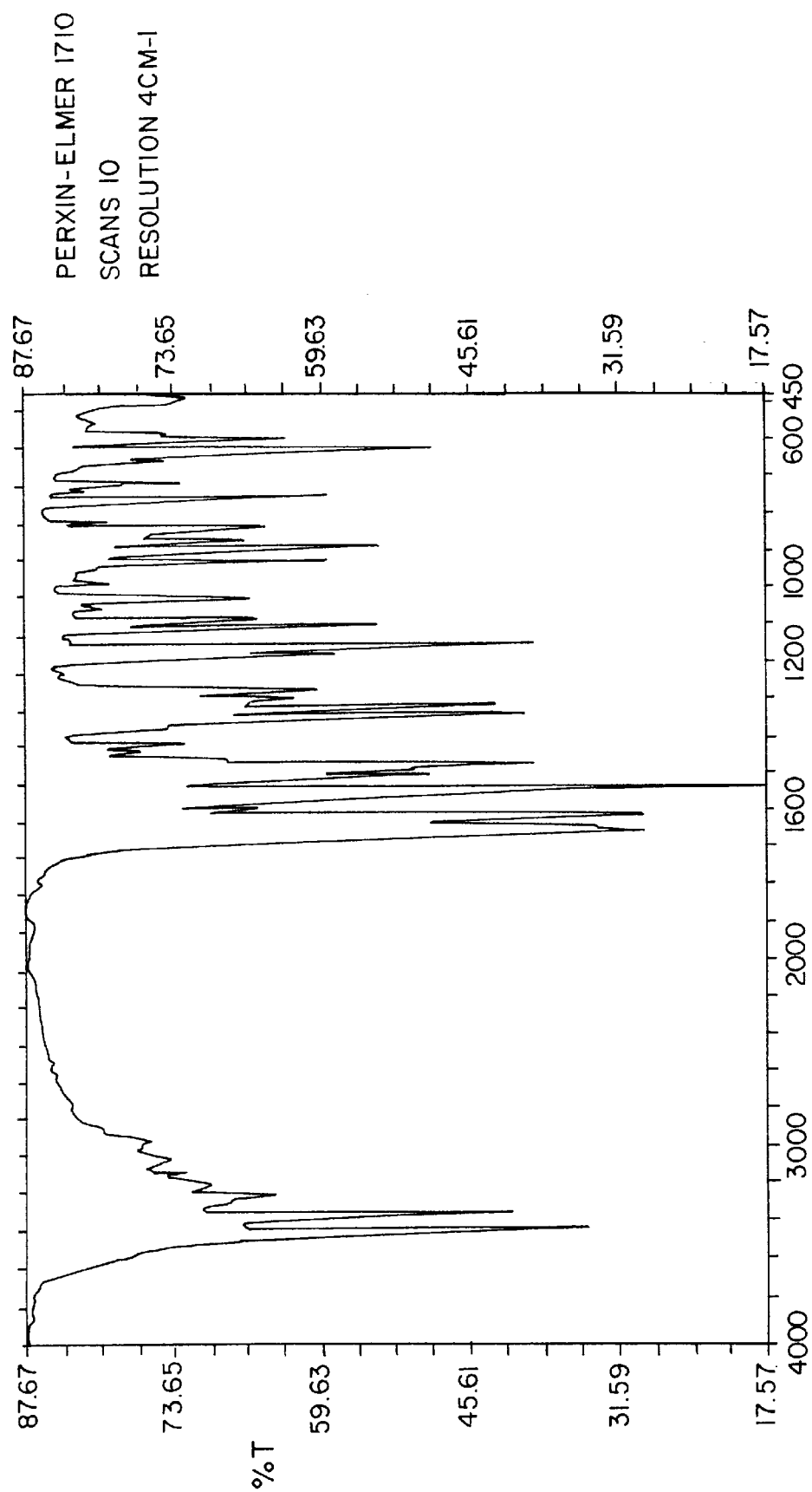
FIG. 4 is a infrared (IR) spectrum of Ebrotidine Form B.

IR (KBr) spectrum: FIG. 4.

Figure 2B:
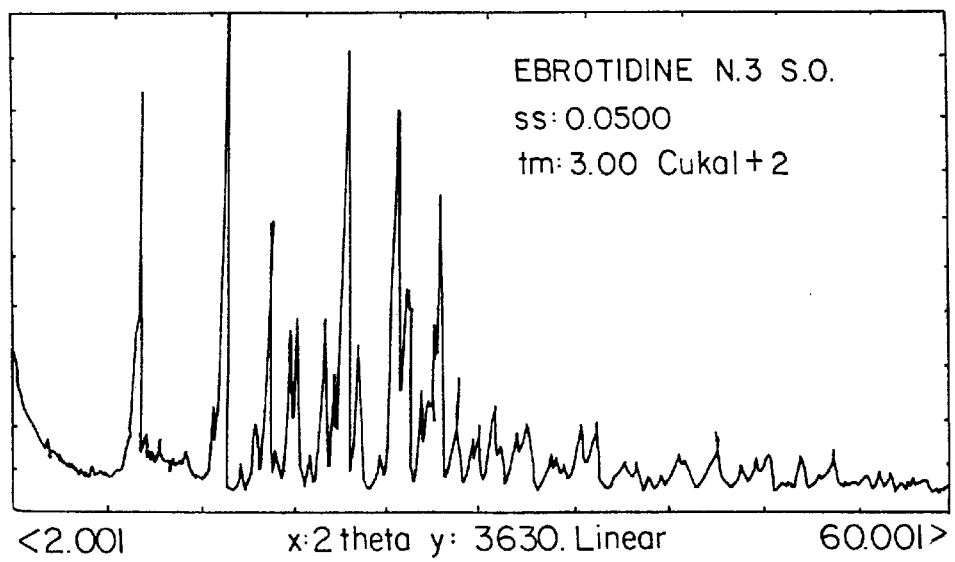

X-ray diffractogram: FIG. 2b.

Differential scanning calorimetry thermogram: FIG. 5.

b) To the filtered methanol solution described in Example 1, some crystals of ebrotidine Form B are added and stirred for 24 hours at room temperature to give 37 g of ebrotidine Form B under the same physicochemical properties of section a).

EXAMPLE 4

Monodose sachets

| | |
|---|---|
| Ebrotidine Form A | 400 mg |
| Ammonium glycyrrhizinate | 120 mg |
| Silicon dioxide | 30 mg |
| Aspartame | 20 mg |
| Corn starch | 1600 mg |
| Scent | 80 mg |
| Sugar to volume | 5000 mg |

EXAMPLE 5

Coated tablets

| | |
|---|---|
| Ebrotidine Form B | 400 mg |
| Croscarmellose sodium | 30 mg |
| Silicon dioxide | 4 mg |
| Magnesium stearate | 12 mg |
| Talc | 60 mg |
| Microcrystalline cellulose | 30 mg |
| Aminoethylmethacrylate copolymer and neutral esters of mathacrylic acid | 8 mg |
| Titanium dioxide | 8 mg |
| Polyethylene glycol 6000 | 2 mg |

We claim:

1. A compound of the chemical name N-[[[2-[[[2-[(diaminomethylene)amino]-4-thiazolyl]methyl]thio]ethyl]amino]methylene]-4-bromo-benzenesulfonamide in Form A having a melting point in the range 74–78° C., the IR spectrum as shown in FIG. 1, the x-ray diffractogram as shown in FIG. 2a and the differential scanning calorimetry thermogram as shown in FIG. 3.

2. A compound of the chemical name N-[[[2-[[[2-[(diaminomethylene)amino]-4-thiazolyl]methyl]thio]ethyl]amino]methylene]-4-bromo-benzenesulfonamide in Form B having a melting point in the range 142.5–146° C., the IR spectrum as shown in FIG. 4, the x-ray diffractogram as shown in FIG. 2b and the differential scanning calorimetry thermogram as shown in FIG. 5.

3. A process for preparing Form A of N-[[[2-[[[2-[(diaminomethylene)amino]-4-thiazolyl]methyl]thio]ethyl]amino]methylene]-4-bromo-benzenesulfonamide of claim 1 which comprises reacting [4-[[(2-aminoethyl)thio]methyl]-2-thiazolyl]guanidine dihydrochloride with ethyl 4-bromo-benzene-sulfonylformimidate in methanol and in the presence of potassium hydroxide, followed by filtering and adding isopropanol over the filtrate to obtain N-[[[2-[[[2-(diaminomethylene)amino]-4-thiazolyl]methyl]thio]ethyl]amino]methylene]-4-bromo-benzenesulfonamide isopropanolate dissolving in methanol, filtering, and adding to water.

4. A process for preparing Form B of N-[[[2-[[[2-(diaminomethylene)amino]-4-thiazolyl]methyl]thio]ethyl]amino]methylene]-4-bromo-benzenesulfonamide of claim 2 which comprises pouring Form A of said compound having a melting point in the range 74–78° C., the IR spectrum as shown in FIG. 1, the x-ray diffractogram as shown in FIG. 2a and the differential scanning calorimetry thermogram as shown in FIG. 3 over methanol; heating the resultant suspension at 50–60° C.; and cooling at room temperature.

5. A process for preparing Form B of N-[[[2-[[[2-(diaminomethylene)amino]-4-thiazolyl]methyl]thio]ethyl]amino]methylene]-4-bromo-benzenesulfonamide of claim 2 which comprises seeding crystals of said Form B compound to a filtrate of N-[[[2-[[[2-(diaminomethylene)amino]-4-thiazolyl]methyl]thio]ethyl]amino]methylene]-4-bromo-benzenesulfonamide isopropanolate; and stirring at room temperature.

* * * * *